United States Patent [19]

Barraud et al.

[11] Patent Number: 4,871,680
[45] Date of Patent: Oct. 3, 1989

[54] PROCESS FOR THE DETECTION OF MOLECULAR OR IONIC SPECIES

[75] Inventors: André Barraud, Bures sur Yvette; Gisèle Derost, Saint Cyr l'Ecole; Laurence Henrion, Boulogne; Annie Ruaudel-Teixier, Verrieres le Buisson, all of France

[73] Assignee: Commissariat a l'Energie Atomique, Paris, France

[21] Appl. No.: 69,248

[22] Filed: Jul. 2, 1987

[30] Foreign Application Priority Data

Jul. 3, 1986 [FR] France ............................ 86 09677

[51] Int. Cl.[4] .......................................... G01N 33/48
[52] U.S. Cl. .................................... 436/103; 436/116; 436/124; 436/150; 436/187
[58] Field of Search ........ 436/103, 113, 116, 124–125, 436/140, 149, 150, 169, 182–183

[56] References Cited

U.S. PATENT DOCUMENTS 4,219,335 8/1980 Ebersole ............................... 422/69
4,511,604 4/1985 Barraud et al. ...................... 118/402
4,632,800 12/1986 Barraud et al. ...................... 118/402

Primary Examiner—Barry S. Richman
Assistant Examiner—Lyle Alfandary-Alexander
Attorney, Agent, or Firm—Michael N. Meller

[57] ABSTRACT

A process and an apparatus for the detection of molecular or ionic species, comprising:

(a) contacting a gaseous or liquid medium containing the species to be detected with a film comprising at least one monomolecular layer of amphiphilic compound chosen from among the tetracyanoquinodimethane (TCNQ) charge transfer complexes and the tetracyanoquinodimethane (TCNQ) salts, which conduct electricity or are precursors of electricity conducting charge transfer complexes and (b) determining the variation of one of the physical properties of the film.

It is in particular possible to use layers of TCNQ alkyl-pyridinium, TCNQ alkyl-quinolinium, for detecting iodine, nitrogen oxides and fluoric compounds.

12 Claims, 1 Drawing Sheet

PROCESS FOR THE DETECTION OF MOLECULAR OR IONIC SPECIES

BACKGROUND OF THE INVENTION

The present invention relates to a process and an apparatus for the detection of molecular or ionic species by a mechanism involving charge transfers.

More specifically it relates to detectors having as active molecules, molecules able to transfer or receive a charge when in contact with the molecular or ionic species to be detected. The operating principle of these detectors is consequently based on redox reactions. The latter can lead to a modification of the electrical conductivity and/or color of the active molecules and this modification can be registered by conventional electrical resistance or optical absorption measuring means.

For some years, detectors of this type have been developed for checking the presence in a gas of molecular species, such as $NO_2$. The article by S. Baker et al published in IEE Proceedings, vol. 130, Part I, no. 5, Oct. 1983, pp. 260–263 illustrates a detector of this type, in which the active molecule is constituted by a copper phthalocyanine of formula: [Cu Pc tris $(CH_2NC_3H_7$-iso)].

This phthalocyanine suffers from the disadvantage of not being depositable in organized monomolecular layer form. Therefore the performance characteristics of the detector are reduced and the reactions between the chemical species to be detected and the active molecules are limited to adsorption or desorption phenomena on the molecular sites of the surface of the film.

SUMMARY OF THE INVENTION

The present invention relates to a process and an apparatus for the detection of molecular or ionic species making it possible to obtain an improved sensitivity and shortened response times, whilst being adapted to the detection of variable quantities of molecular or ionic species. The process comprises:

(a) contacting a gaseous or liquid medium containing the species to be detected with a film comprising at least one monomolecular layer of an amphiphilic compound chosen from among the tetracyanoquinodimethane charge transfer complexes (TCNQ) and the tetracyanoquinodimethane salts (TCNQ), which conduct electricity or are precursors of electricity conducting charge transfer complex and
(b) determining the variation of one of the physical properties of the film.

Generally the film is formed from several monomolecular layers and in this case most frequently several monomolecular layers of the same compound are used.

However, it is also possible to use a film formed from monomolecular layers alternately constituted by a monomolecular layer of said compound and a monomolecular layer of another amphiphilic compound.

According to the invention, the nature of the compounds used for producing the monomolecular layers is chosen as a function of the chemical species to be detected.

The chemical species to be detected can be constituted by molecules or ions able to give rise to redox reactions. These species can be in a gaseous or liquid medium, e.g. in an aqueous solution, in air, or in other gases. During the contacting of the gaseous or liquid medium with the film, the redox reaction takes place and leads to a modification of the physical properties of the film.

Examples of chemical species which can be detected in a gaseous medium by the process according to the invention are halogens and in particular iodine, oxygen, fluorine compounds such as $AsF_5$, $BF_3$ and $PF_5$, nitrogen oxides of formula $NO_z$ in which z is a number between 1 and 3, ammonia and benzene. The chemical species which can be detected in the liquid medium are e.g. acids, such as hydrochloric and acetic acids.

When use is made of a film alternately formed from monomolecular layers of different compounds, the second compound can also be a TCNQ charge transfer complex or a TCNQ salt, which conducts electricity or is a precursor of a conducted charge transfer complex, but it can also be constituted by other conductive or insulating amphiphilic compounds, such as behenic acid.

It is pointed out that the term amphiphilic or amphipathic compound is understood to refer to organic molecules having a hydrophobic part, i.e. a part having a repulsion for polar liquids such as water and a hydrophilic part, i.e. a part having an affinity for polar liquids such as water.

In the process according to the invention, use is made of TCNQ charge transfer organic complexes or TCNQ salts which conduct electricity or are precursors of electricity conducting charge transfer organic complexes made amphiphilic, which e.g. comprise at least one saturated or unsaturated hydrocarbon substituent with at least 12 carbon atoms and at least one polar group.

The compounds usable in the invention are TCNQ organic charge transfer complexes and TCNQ salts, where there is a displacement of the equilibrium under the action of the species to be detected. These compounds conduct electricity, or are precursors of electrically conducting charge transfer complexes.

It is pointed out that charge transfer complexes are formed by the association of two molecules, whereof one, A, acts as an electron acceptor and the other, D, acts as an electron donor. It is possible to represent this reaction in the following way:

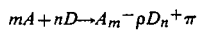

m and n representing the respective numbers of molecules and $\rho$ the charge transfer corresponding to the proportion of transferred electrons.

If m=n, there is a simple stoichiometry and if m differs from n, there is a complex stoichiometry.

If $\rho$ is substantially equal to 0, the complex is a molecular complex with a neutral fundamental state. If $\rho$ is equal to 1, i.e. a true ionic compound with one electric charge per molecule D or A and if $\rho$ is below 1, there are less electric charges than molecules present. Thus, there is a mixed valence compound, which is the condition necessary for obtaining an organic conductor. Thus, a distinction can be made between:

(1) true charge transfer complexes in which there is a transfer of an electron from the donor to the acceptor, said single electrons then being on $\pi$ orbitals ($\pi$-$\pi$ complexes) and
(2) salts of radical ions, in which only one of the ions is of a radical nature, the counterion being diamagnetic.

Complexes of this type are more particularly described in Annales de Physique, 1976, vol. 1, no. 4–5, pp. 145–256 and in Journal de Chimie Physique, 1982, 79, no. 4.

TCNQ charge transfer complexes and TCNQ salts, which conduct electricity or which are precursors of electrically conducting complexes usable in the invention can be the compounds described in European patent application Nos. 161 987 and 165 111 filed in the name of the Commissariat a l'Energie Atomique.

These complexes and amphiphilic salts of TCNQ can be in accordance with the following formula:

$$DA_xX_y \qquad (I)$$

in which D represents an organic monomeric electron donor group, A represents 7,7,8,8-tetracyanoquinodimethane or one of its substituted derivatives, X represents a non-amphiphilic electron acceptor chosen from among the Lewis acids, x is a number equal or exceeding 1 and y is equal to 0 or is a number exceeding 0, at least one of the groups D and A being amphiphilic and having at least one saturated or unsaturated hydrocarbon substituent with at least 12 carbon atoms. Generally, x and y can assume values up to 20. Preferably, the hydrocarbon substituent has 14–30 carbon atoms.

In the above formula, X advantageously represents a Lewis acid chosen from among $PF_6^-$, $ClO_4^-$, $ReO_4^-$, $IO_4^-$, $FSO_3^-$, $AsF_6^-$, $AsF_4^-$, $Br^-$, $Cl^-$, $MnCl_6^-$, the iodides and nitrogen oxides of formula $NO_z$, with z varying between 1 and 3.

When the organic monomeric electron donor group D is an amphiphilic group, the latter can be constituted by an aliphatic, aromatic or heterocyclic base having at least one saturated or unsaturated, hydrocarbon substituent with at least 12 carbon atoms.

Among the aliphatic bases which can be used, are quaternary ammonium groups of formula:

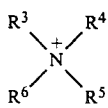

in which $R^3$, $R^4$, $R^5$ and $R^6$, which can be the same or different, are alkyl radicals or hydrocarbon chains optionally having one or more double and/or triple bonds, whereby at least one of the groups $R^3$, $R^4$, $R^5$ and $R^6$ has at least 12 carbon atoms.

The aromatic bases which can be used can be advantageously constituted by quaternary ammonium groups derived from aniline or substituted derivatives of aniline.

The heterocyclic bases which can be used can be constituted by quaternary ammonium groups derived from pyridines, piperidines, bipyridines, benzopyridines, e.g. quinolines, isoquinolines, acridines, phenazines and phenanthronlines.

Examples of such bases are alkyl-N-alkylisonicotinates, which can be obtained by esterifying the pyridine-4-carboxylic acid by a fatty alcohol of formula R'OH, in which R' is an alkyl radical with 16–30 carbon atoms and by then quaternizing the ester by an alkyl halide of formula $C_nH_{2n+1}X$, in which n is an integer between 1 and 4 and X represents Cl, Br or I.

To then obtain the TCNQ alkyl-N-alkylisonicotinates, the isonicotinate is reacted with the tetracyanoquinodimethane lithium salt.

The group D can also be constituted by tetrathiofulvalene (TTF) or tetraselenafulvalene (TSF) or members derived from this family, such as e.g. tetramethyl-TTF (TMTTF), TMTSF, bis-ethyl-dithio-TTF (BEDT-TTF), etc.

The group D can also represent a heterocyclic base having several heteroatoms of different natures, e.g. nitrogen and sulphur atoms. Examples of such heterocyclic bases are N-alkylbenzothiazoles and their substituted derivatives and N-alkylindoleniniumtrimethinecyanines and their substituted derivatives. The group D can be also constituted by derivatives of the sulphonium and phosphonium type, e.g. trialkylsulphonium and tetraalkylphosphonium groups.

TCNQ trialkylsulphonium can be obtained by quaternizing dialkyl sulphide of formula

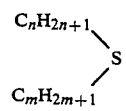

in which n and m are integers between 2 and 30 by an alkyl halide of formula $C_{n'}H_{2n'+1}X$, in which n' is an integer between 16 and 30 and X represents Cl, Br or I, in order to obtain a trialkylsulphonium halide, which is then reacted with the tetracyanoquinodimethane lithium salt, which makes it possible to obtain TCNQ trialkylsuphonium.

TCNQ tetraalkyphosphonium can be obtained from trialkyl phosphines of general formula $(C_nH_{2n+1})_3P$, in which n is an integer between 2 and 30, and the three alkyl groups can be different by quaternizing these trialkylphosphines in an anhydrous medium by a alkyl halide of formula $C_{n'}H_{2n'+1}X$, in which n' is an integer between 16 and 30 and X represents Cl, Br or I to obtain the tetraalkylphosphonium halide, which is then reacted with the tetracyanoquinodimethane lithium salt to obtain the corresponding TCNQ tetraalkyphosphonium.

It is pointed out that within the terms of the present text "saturated or unsaturated hydrocarbon radical" designates radicals formed from atoms of carbon and hydrogen optionally incorporating one or more double and/or triple bonds. The latter can be connected to the electron acceptor group A and/or to the electron donor group D by a single bond, heteroatom or another organic function (ester, ... ).

In these amphiphilic complexes, the group A is TCNQ or one of the substituted derivatives thereof or from the group of N, N' dicyanoquinodiimine. Examples of such derivatives are halogen derivatives, such as fluorine derivatives, alkoxis derivatives and alkyl derivatives, such as e.g. $C_{18}$ or $C_{22}$ monoalkyl TCNQ.

The TCNQ complexes and salts of formula $DA_x$, such as TCNQ-alkylpyridinium, TCNQ-alkylquinolinium, TCNQ-alkylammonium, TCNQ-alkylsulphonium, TCNQ-alkylphosphonium and TCNQ-alkyl-N-alkylisonicotinate can be used in particular for the detection of chemical species able to react with complexes of formula $DA_x$ to form complexes of formula $DA_xX_y$.

For example, the species can be halogens, such as iodine, fluorine compounds such as $AsF_5$, $BF_3$ and $PF_5$ and nitrogen oxides of formula $NO_2$ with z being between 1 and 3.

In this case, the initial complexes which were not electrically conducting become conductors by reacting with the species to be detected and it is possible to verify the presence or absence of the species to be detected by determining the variation of the electrical resistance of the film.

However, in most cases, this reaction of the species with the film also leads to a change in the color of said film, which can be followed by determining the optical absorption.

The electrically conducting charge transfer complexes of formula $DA_xX_y$ can be used for the detection of chemical species reacting with these complexes to make them insulating or to improve their electrical conductivity.

For example, the species to be detected can be ammonia, nitrogen oxides of formula $NO_z$ and benzene. The complexes used can in particular be TCNQ-alkylpyridinium iodides.

It is also possible to use these complexes in association with non-electrically conducting amphiphilic molecules, which is the case e.g. with films constituted by monomolecular layers alternately formed by TCNQ-alkylpyridinium and behenic alcohol.

The charge transfer complexes described hereinbefore can be prepared by conventional processes, like that described by L. R. Melby et al in Journal of Am. Chem. Soc., vol. 84, 1962, pp. 3374–3387.

The use in the invention of a film formed from monomolecular layers makes it possible to obtain numerous advantages. Thus, the sensitivity is improved on the response times shortened due to the structure and organization of the molecules in the film. The film can be adapted to the number of species to be detected, e.g. by increasing the number of monomolecular layers with the quantity to be detected, in order to obtain a stoichiometric reaction of the molecules of the film with a species to be detected. In such a structure, the molecular or ionic species diffuse within this film. Thus, a mass phenomenon is obtained and not merely the surface phenomenon observed with cooper phthalocyanine described by Baker, which is not an amphiphillic molecule and can therefore not be deposited by the Langmuir Blodgett method in the form of organized monomolecular layers.

The invention also relates to detection apparatuses using TCNQ charge transfer complexes and TCNQ salts, which conduct electricity or which are precursors of electrically conducting charge transfer complexes.

These apparatuses comprise a support coated with a film incorporating at least one monomolecular layer constituted by the aforementioned amphiphilic compounds and can be designed for effecting detection by determining the electrical resistance of the film.

In this case, the apparatus comprises electric contacts making it possible to effect the electrical measurement of the film and the support is made from an electrically insulating material. These supports are generally amorphous supports, e.g. of glass, $F_2Ca$ or quartz. It is also possible to use organic polymer supports, e.g. of Mylar.

The detection apparatus can also comprise an intermediate adhesion promoting layer located between the support and the film formed from the monomolecular layers of layer. This adhesion promoter makes it possible to improve the adhesion of the film to the support, when the latter does not have an adequate affinity for the molecules constituting the monomolecular layers.

The intermediate layer of this adhesion promoter is preferably constituted by one or more monomolecular layers of an amphiphilic compound, which can be in particular a fatty acid, such as $\omega$-triconsenoic acid, behenic acid or other molecules of amphiphilic compounds making it possible to establish the bond between the support and the active molecules.

In order to produce the detectors according to the invention, the monomolecular layers are deposited on the support by the known Langmuir Blodgett method described in J. of Am. Chem. Soc., vol. 57, 1935, pp. 1007–1010. The apparatuses used for these deposits are of a conventional nature and can in particular be the vessel described in French patent application No. 2 556 244 or that described in French Patent No. 2 341 199.

When it is wished to deposit alternate layers, i.e. successive monomolecular layers produced with different molecules, it is possible to use the vessel described in French Patent No. 2 541 936.

When the detection apparatus comprises electrical contacts for measuring an electrical property of the film, they are generally produced on the insulating support prior to the deposition of the layers. This can be carried out by depositing on certain parts of the insulating support, i.e. at the locations chosen for the production of the electrodes, strips of carbon or gold, which are then covered with a conductive paste, such as a gold or silver paste, in which is immersed a conductive metal wire.

It is firstly possible to deposit on the insulating support the conductive paste in accordance with the desired alignments and then cover the substrate at points defining the electrodes with a carbon or gold coating.

Using the detection apparatus according to the invention, it is possible to follow different properties of the film, which are generally electrical properties and/or optical properties.

In the case where it is wished to follow an electrical property, such as the conductivity, it is possible to have three variation types as a function of the nature of the molecules used for producing the film.

(1) The film can be conductive and, after reaction with the species to be detected, can either come more conductive or less conductive.

(2) The film can be conductive, but become insulating after reaction with the species to be detected.

(3) The film can be insulating and become conductive after reaction with the species to be detected.

Thus, in all these cases it is appropriate to be able to measure the resistance variation of the film. To carry out this measurement, it is possible to use various arrangements. Generally, in order to improve accuracy, a differential measurement is carried out between a detector placed in the medium to be controlled and a detector placed in a reference medium. This can be brought about by using a single support on which are arranged a first reference film in contact with the air or a reference gas, and a second identical film in contact with the medium containing the species to be detected.

According to the invention, the physical property to be checked can also be an optical property, such as a color change. In this case, it is possible to use optical absorption measurements at one or more wavelengths characteristic of the molecules constituting the film, said wavelengths being able to correspond to the appearance of a complex, the disappearance of an absorption band, or the displacement of absorption bands due to the redox reaction.

It is preferable to use for each wavelength a light-emitting diode, optionally equipped with filters and a photoelectric transducer or sensor.

In order to improve selectivity and ensure that no undesirable species are obtained, simultaneous measurement can take place at several wavelengths by using a set of light-emitting diodes and photoelectric cells functioning either on the same film, or on several films, which can be disposed on the same insulating support.

As hereinbefore, it is also possible to perform each of the measurements in the form of a differential measurement using two detection apparatuses, whereof one is in contact with the chemical species to be detected and the other is in contact with a reference medium.

According to the invention, it is also possible to carry out detection by simultaneously measuring the variations of the optical properties and electrical properties. In this case, it is possible to use several different detection apparatuses.

In the case where the change of color of the film by reaction with the species to be detected is very clearly defined, it is possible to simplify the detection mode by using a film deposited on a support and standards indicating the color change of the film as a function of the species to be detected and their quantities. In this case, it is merely necessary to compare the film with the strip of standards.

BRIEF DESCRIPTION OF THE DRAWINGS

The invention is described in greater detail hereinafter relative to non-limitative examples and the attached drawings, wherein.

DESCRIPTION OF EXAMPLES

Example 1

Figure 1:
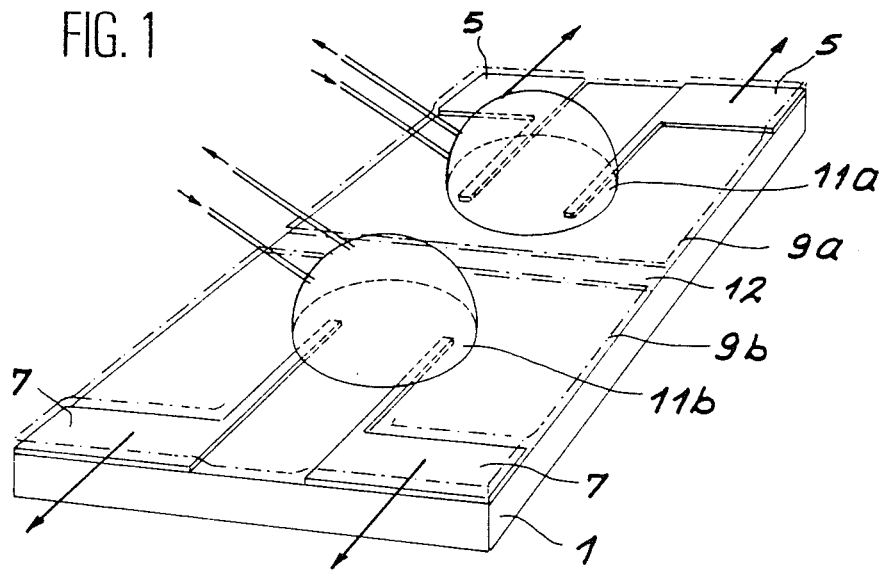
FIG. 1 is a perspective view of an apparatus for the differential measurement of an electrical property of a transducer or sensor according to the invention.

This example illustrates the use of a detector having a film formed from several monomolecular layers of $TCNQ^-$ docosylpyridinium for the detection of iodine.

The $TCNQ^-$ docosylpyridinium is prepared by metathesis on the basis of N-docosylpyridinium iodide and TCNQ lithium salt operating in an alcoholic medium and then recrystallizing the complex in ethanol.

On a rectangular fluorine plate is placed a mask, so as to mask the central part of the plate. Carbon is then deposited by evaporation, in order to obtain two parallel carbon strips 8 mm apart on two opposite sides of the plate. Electric contacts are then formed on the carbon strips by depositing at one of the ends of the support on each carbon strip, silver conductive paste marketed under the trademark Epotek and in this paste is immersed a metal wire for forming the electric contacts. The mask is then removed and over the entire plate surface are deposited two monomolecular layers of an adhesion promoter constituted by behenic acid using the Langmuir Blodgett method and the Optilas LB 105 vessel described in French Patent No. 2 556 244. The behenic acid is in $10^{-3}$ mol.l$^{-1}$ solution in chloroform and is progressively compressed for deposition at a pressure of 35 mN.m$^{-1}$.

This operation is followed by the deposition of 20 layers of $TCNQ^-$ N-docosylpyridinium amphiphilic complex using the same equipment and a $10^{+3}$ mol.l$^{+1}$ solution of the complex in a dichloromethaneethanol mixture and by progressively compressing the layer to a pressure of 35 mN.m$^{-1}$.

Following the deposition of the 20 layers, the resistance of the film is measured at the terminals of the two carbon strips and this demonstrates that the film is insulating, the resistance exceeding $10^{10}$ ohms.

The film is then exposed to iodine vapours and the electrical resistance of the film instantaneously drops and stabilizes at values between $10^7$ ohms and $60.10^7$ ohms for iodine contents between 20 and 100 ppm. These measurements correspond to a resistivity of approximately $10^2$ ohms.cm.

It is also possible to detect the presence of iodine by an optical measurement. Thus, in the presence of iodine, the optical density of the film at 675 nm (absorption band corresponding to the dimer $TCNQ_2^{2-}$) progressively drops and the obtained product absorbs on the whole specturm.

Example 2

This example illustrates the use of the detector of Example 1 for the detection of $NO_z$ vapours. In this case, for $NO_z$ quantities of 0.5%, a resistance of $10^7$ ohms is obtained, which gives a resistivity of $10^2$ ohms.cm and corresponds to a good conducting film. It is also possible to carry out the measurement by observing the colour change of the film from blue to violet.

Example 3

In this example use is made of $TCNQ^-$ N-docosylpyridinium for the detection of iodine, ammonia or nitrogen oxides using a special arrangement for carrying out a differential measurement. In this case, two detectors are formed on the insulating fluorine plate of FIG. 1, so that the reference detector and the true detector are present on the same support.

This arrangement is shown in FIG. 1, where it can be seen that the insulating support 1 is provided at either end of the plate with two sets of electric contacts 5,7. The plate is covered with 2 monomolecular layers of $TCNQ^-$ N-docosylpyridinium forming film 9, which has been subdivided into two parts, namely 9a and 9b respectively corresponding to the reference detector and to the true detector.

On part 9a of the film can be placed a cup or capsule 11a, whilst effecting sealing by means of a Viton VT 70 joint and said cup is provided with supply and discharge pipes making it possible to circulate a reference gas, such as nitrogen therein. On part 9b of the film is also placed an identical cup 11b, which is tightly mounted on the film by means of a Viton joint and which is equipped with gas supply and discharge pipes making it possible to circulate the gaseous medium containing the species to be detected therein.

Figure 2:
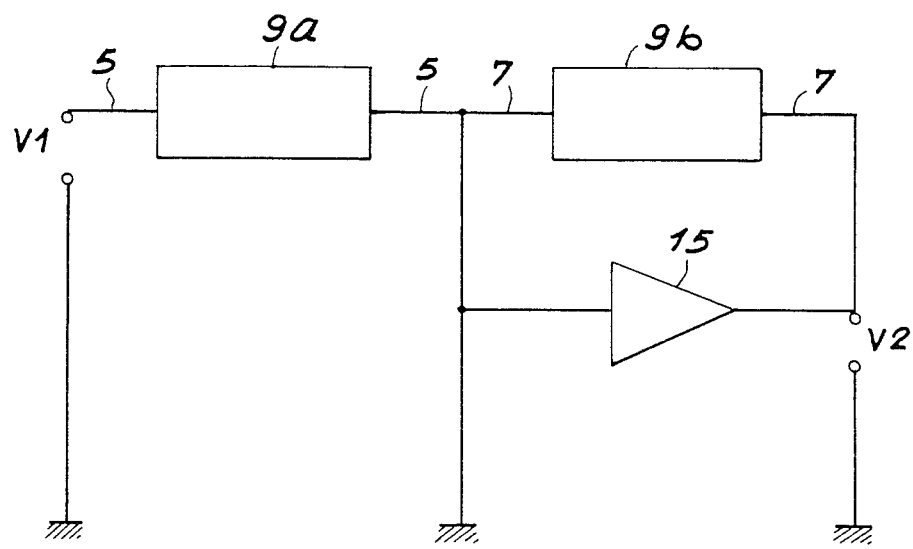
FIG. 2 shows diagrammatically the differential arrangement of the two detectors of the apparatus of FIG. 1.

In order to construct this device, firstly there are deposited silver paste lines on the insulating support making it possible to effect electric contacts outside cups 11a and 11b. This is followed by the deposition by evaporation of the carbon or gold with masks in order to define the two sets of electrodes 5 and 7, followed by the deposition on the plate of two monomolecular layers of $TCNQ^-$ N-docosylpyridinium, as in Example 1. The two detectors of the apparatus of FIG. 1 are connected to an electric circuit in accordance with the differential arrangement of FIG. 2, which shows the same references as those of FIG. 1. Thus, it is possible to see the reference detector 9a and the actual detector 9b mounted by means of their output terminals 5 and 7 at the terminals of amplifier 15, which makes it possible to measure the voltages $V_1$ and $V_2$ at the terminals of the two detectors.

The measurements initially performed on the two sets of electrodes show that the film is insulating. The film is then doped with iodine and this leads to a conductive film with a resistance of $2.10^8$ ohms. The two detectors are then insulated by placing the cups on the film and scratching the latter between the two cups (at 12). The gaseous mixture to be controlled is then introduced into cup 11b and an inert gas into cup 11a. When the gas to be detected is ammonia, the resistance increases very rapidly in detector 11a for which it is $6.10^8$ ohms, whereas it remains at $2.10^8$ ohms in the reference detector. On continuing the action of ammonia, the resistance further rises to $10^{9''}10^{10}$ ohms and the film becomes insulating. Moreover, the film which was green under the action of iodine becomes blue again.

Conversely, on using this arrangement for detecting a nitrogen oxide, the resistance decreases in the detector, because the conductivity of the film exposed to nitrogen oxide increases.

Example 4

This example makes use of a film formed from alternating layers of TCNQ$^-$ N-docosylpyridinium and behenic alcohol with 16 layers in all and which was doped with iodine, in order to detect benzene vapours.

Use is made of a quartz insulating support and the alternate layers of TCNQ$^-$ N-docosylpyridinium and behenic alcohol are deposited using the vessel described in French Patent No. 2 541 936. This is followed by the doping of the film with iodine and its resistance is measured and is $5.3.10^8$ ohms.

When this film is exposed to benzene vapours, an electrical resistance of $6.1 \cdot 10^8$ ohms is obtained and on continuing this benzene vapour exposure, the film becomes insulating.

It is also possible to detect the benzene vapours by observing the colour change of the film, which passes from violet to pale blue. The optical density drops in a marked manner at 395 nm and there is a shoulder at 410 nm.

Example 5

This examples makes use of a TCNQ N-docosylquinolinium film for the detection of fluoric products, such as AsF$_5$, BF$_3$ and PF$_5$.

Two layers of $\omega$ tricosenoic acid from a $10^{-3}$ mol.l$^{-1}$ $\omega$-tricosenoique acid in chloroform are firstly deposited on a glass support using the Langmuir Blodgett method, whilst compressing to a value of 32.5 mN.m$^{-1}$. This is followed by the preparation of TCNQ N-docosylquinolinium by reacting 1 mmole of N-docosylquinolinium iodide with 1 mmole of TCNQ lithium salt. A $10^{-3}$ mol.l$^{-1}$ solution used for depositing four TCNQ N-docosylquinolinium monomolecular layers on the glass support coated with two $\omega$ tricosenoic acid layers and whilst effecting compression to a value of 30 mN.m$^{-1}$.

When the thus obtained film is contacted with traces of AsF$_5$ or other fluoric products, such as BF$_3$ or PF$_5$ in a vacuum enclosure, a color change is observed. Thus, the film which was blue, instantaneously becomes yellow. This modification of the optical properties of the film can be observed at 680 and 380 nm.

Example 6

This example uses TCNQ N-octadecylpyridinium for the detection of NO$_z$ vapours. This complex is firstly synthesized by hot reacting in an alcoholic solution N-octadecylpyridinium iodide with the tetracyanoquinodimethane lithium salt.

Thus, after cooling, a powder is obtained, which is washed and recrystallized. This powder is then redissolved in acetonitrile with a TCNQ equivalent. A black complex crystallizes cold, is an electrical conductor and complies with formula:

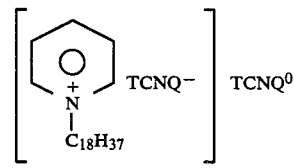

Then, as in Example 1, a rectangular fluorine plate is prepared, which has electric contacts and two monomolecular layers of behenic acid and on said plate are deposited 30 superimposed monomolecular layers of the complex TCNQ N-octadecylpyridinium salt using a $5.10^{-4}$ mol/l solution of said complex salt in chloroform and accompanied by compressing at a pressure of 32.5 mN.m$^{-1}$.

The electrical conductivity of the film is then determined and it is exposed to dry air containing 22 ppm of NO$_z$ vapours. Under these conditions, the electrical conductivity variation is 20% in 30 s and 58% in 5 min. When the detector is exposed to dry air containing 200 ppm of NO$_z$ vapours, the electrical conductivity variation is 26% in 30 s and 99% in 10 min.

Example 7

In this example, use is made of TCNQ diethyldocosylsulphonium for detecting the presence of iodine vapours. The TCNQ diethyldocosylsulphonium is firstly prepared in the following way.

Diethyl sulphide is quaternized by docosyl iodide in order to obtain diethyldocosylsulphonium iodide. This iodide is then placed in an alcoholic solution with an equivalent of the TCNQ lithium salt. This gives crystals, which are recrystallized in alcohol. These crystals are constituted by the simple tetracyanoquinodimethane diethyl docosyl sulphonium salt of formula:

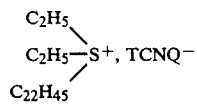

As in example 1, a fluorine plate is then prepared, which is equipped with electric contacts and a film formed from 100 monomolecular TCNQ diethyldocosylsulphonium layers is deposited thereon. In order to bring about the deposition of the film, one part of TCNQ diethyldocosylsulphonium is mixed with one part of octadecyl urea in chloroform and compression takes place at 30 mN.m$^{-1}$. Thus, 100 layers are transferred to the fluorine plate. The film obtained is blue and insulating.

It is then exposed to iodine vapours, changes color and assumes a violet shade. The infrared spectrum is that of a metallic conductor and there is resistivity of $10^2$ ohms.cm.

Example 8

This example uses tetracyanoquinodimethane triethyl docosylphosphonium for detecting the presence of iodine. Firstly triethyl docosylphosphonium bromide is prepared by reacting triethylphosphine with docosyl bromide. The triethyldocosylphosphonium bromide is then dissolved in alcohol and is reacted with an equivalent of the TCNQ lithium salt. This gives crystals which are recrystallized in alcohol and comply with the formula:

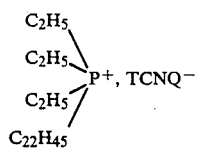

As in Example 1, a fluorine plate provided with electric contacts is prepared and on said plate is deposited a film formed from two monomolecular layers of said salt, effecting the deposition of the layers on the fluorine plate from a complex solution in chloroform and whilst carrying out compression at a pressure of 25 mN.m$^{-1}$.

The deposition of the two layers is followed by the measurement of the resistance of the film. It is found that the film is insulating and blue. This film is then exposed to iodine vapours. Its colour changes to violet and its infrared spectrum reveals electronic conductivity properties.

Example 9

This example uses docosyl N-methylisonicotinate for detecting the presence of iodine. The complex is firstly prepared from pyridine-4-carboxylic acid, which is esterified by docosanol.

This gives docosyl isonicotinate, which is quaternized by methyl iodide. The thus obtained quaternary salt is brought into alcoholic solution with one equivalent of TCNQ lithium salt, which gives the salt of formula:

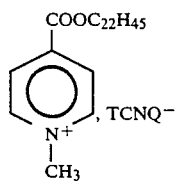

which is recrystallized in alcohol.

As in Example 1, a fluorine plate is prepared, which has electric contacts and two behenic acid layers. On the plate is deposited a film formed from 26 monomolecular layers of said salt from a solution thereof in dichloromethane containing 5% ethanol, carrying out compression under a pressure of 35 mN.m$^{-1}$.

The resistance of the film is measured and is found to be insulating. Its color is blue. The film is exposed to iodine vapours, its color changes to violet and its resistance drops instantaneously, because the film becomes conductive.

Example 10

This example makes use of TCNQ trimethyldocosylammonium for detecting the presence of iodine.

Firstly, the trimethyldocosylammonium iodide is prepared from trimethylamine by reacting it with docosyl iodide and is then recrystallized in alcohol. This iodide is placed in alcoholic solution with one equivalent of the tetracyanoquinodimethane lithium salt and a precipitate of the single salt is obtained:

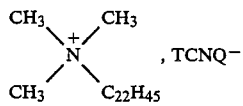

As in Example 1, a fluorine plate is prepared, which has electric contacts and two behenic acid layers. On this plate is deposited a film formed from six monomolecular TCNQ trimethyldocosylammonium layers using a solution of the salt in chloroform and whilst compressing it under a pressure of 24 mN.m$^{-1}$.

After the deposition of six layers, the resistance of the film is measured and is found to be insulating. The film is then exposed to iodine vapours. Its resistance drops instantaneously and the film becomes conductive.

What is claimed is:

1. A process for the detection of molecular or ionic species present in a gaseous or liquid medium which comprises:
   (a) contacting said gaseous or liquid medium with a film comprising at least one monomolecular layer of an amphiphilic tetracyanoquinodimethane (TCNQ) compound selected from the group consisting of electrically conductive tetracyanoquinodimethane (TCNQ) charge transfer complexes, electrically conductive tetracyanoquinodimethane (TCNQ) salts, electrically insulating (TCNQ) charge transfer complexes capable of becoming electrically conductive by reaction with the molecular or ionic species to be detected, and electrically insulating (TCNQ) salts capable of becoming electrically conductive by reaction with the molecular or ionic species to be detected, and
   (b) measuring the change in electrical resistance of the film contacted with said medium.

2. A process according to claim 1, wherein the film is formed from several monomolecular layers alternately constituted by a monomolecular layer of said amphiphilic (TCNQ) compound and a monomolecular layer of another amphiphilic compound selected from the group consisting of amphiphilic fatty acids and fatty alcohols.

3. A process according to claim 2, wherein the film is constituted by monomolecular layers formed alternately from a first compound constituted by a TCNQ alkyl-pyridinium iodide and a second compound constituted by behenic alcohol.

4. A process according to claim 1, wherein the amphiphilic (TCNQ) compound has the formula DA$_x$X$_y$, in which D represents an organic monomeric electron donor group, A represents 7,7,8,8-tetracyanoquinodimethane or 7,7,8,8-tetracyanoquinodimethane substituted by substituents selected from the group consisting of halogen atoms, alkyl radicals and alkoxy radicals, X represents a non-amphiphilic electron acceptor Lewis acid, x is number equal to 1 or exceeding 1 and y is equal to b 0 or is a number exceeding 0, at least one of the groups D and A being amphiphilic and having at least one alkyl, alkenyl or alkynyl substituent having at least 12 carbon atoms.

5. A process as in claim 4, wherein the film is constituted by monomolecular layers formed alternately from a first compound constituted by a TCNQ alkyl-pyridinium iodide and a second compound constituted by behenic alcohol.

6. A process according to claim 4, wherein said amphiphilic TCNQ compound is selected from the group consisting of TCNQ alkyl-ammonium, TCNQ alkyl-pyridinium, TCNQ alkyl-quinolinium, TCNQ alkyl-sulphonium, TCNQ alkyl-phosphonium and TCNQ alkyl-N-alkylisonicotinates.

7. A process according to claim 6, wherein the species to be detected is selected from the group consisting of iodine $AsF_5$, $BF_3$ and $PF_5$, nitrogen oxides of formula $NO_z$, with z being between 1 and 3.

8. A process according to claim 4, wherein the TCNQ compound is a TCNQ alkyl-pyridinium iodide.

9. A process according to claim 8, wherein the species to be detected is selected from the group consisting of ammonia, a nitrogen oxide of formula $NO_z$ wherein z is between 1 and 3, and benzene.

10. A process for the detection of molecular or ionic species present in a gaseous or liquid medium which comprises:

(a) contacting said gaseous or liquid medium with a film comprising at least one monomolecular layer of an amphiphilic tetracyanoquinodimethane (TCNQ) compound selected from the group consisting of electrically conductive tetracyanoquinodimethane (TCNQ) charge transfer complexes, electrically conductive tetracyanoquinodimethane (TCNQ) salts, electrically insulating (TCNQ) charge transfer complexes capable of becoming electrically conductive by reaction with the molecular or ionic species to be detected, and electrically insulating (TCNQ) salts capable of becoming electrically conductive by reaction with the molecular or ionic species to be detected, and (b) measuring the change optical absorption of the film contacted with said medium.

11. A process according to claim 10, wherein the film is formed from several monomolecular layers alternately constituted by a monomolecular layer of said amphiphilic (TCNQ) compound and a monomolecular layer of another amphiphilic compound selected from the group consisting of amphiphilic fatty acids and fatty alcohols.

12. A process according to claim 11, wherein the film is constituted by monomolecular layers formed alternately from a first compound constituted by a TCNQ alkyl-pyridinium iodide and a second compound constituted by behenic alcohol.

* * * * *